United States Patent [19]

Albrecht et al.

[11] Patent Number: 5,798,247

[45] Date of Patent: Aug. 25, 1998

[54] ORGANIC-CHEMICAL COMPOUND WITH ICE-INHIBITORY ACTION

[75] Inventors: Hans-Peter Albrecht, Gorxheimertal; Hans-Joachim Böhm, Limburgerhof, both of Germany; Kenneth Dale Brady, Worcester, Mass.; Peter Eckard, Weinheim; Kurt Ritter, Heidelberg, both of Germany; Robert Vincent Talanian, Needham, Mass.; Nigel Walker, Dossenheim, Germany

[73] Assignee: BASF Aktiengesellschaft, Ludwigshafen, Germany

[21] Appl. No.: 821,605

[22] Filed: Mar. 20, 1997

Related U.S. Application Data

[62] Division of Ser. No. 498,972, Jul. 6, 1995, abandoned, which is a division of Ser. No. 239,324, May 6, 1994, abandoned.

[51] Int. Cl.$^6$ .............................. C12N 9/48; A61K 38/00
[52] U.S. Cl. ........................ 435/212; 435/219; 435/226; 514/19
[58] Field of Search ................................ 435/219, 212, 435/226; 514/19

[56] References Cited

U.S. PATENT DOCUMENTS 5,434,248  7/1995  Chapman et al. ..................... 530/330
5,462,939  10/1995 Dolle et al. ......................... 514/231.5

OTHER PUBLICATIONS

Journal of Computer–Aided Molecular Design, 6(1992)593–606.

Journal of Computer–Aided Molecular Design,6(1992) 61–78.

Structure–Based Strategies for Drug Design and Discovery, Kuntz, 1078–1082, Science, vol. 257, Aug. 21, 1992.

Journal of Medicinal chemistry, vol. 34, No. 7, Jul. 1991, 1925–1934.

Sleath et al. J. Biol. Chem. vol. 265 No. 24 (Aug. 1990) 14526–28.

Science vol. 256 24 Apr. 1992 p. 441.

Hardtmann et al. J. Med. Chem 1969 12(5) 1093–6 & Abstract.

*Primary Examiner*—Cecilia J. Tsang
*Assistant Examiner*—Bennett Celsa
*Attorney, Agent, or Firm*—Keil & Weinkauf

[57] ABSTRACT

Organic chemical compounds with ICE-inhibitory action which have structures such that they enter into an interaction with binding sites in a binding cavity.

9 Claims, No Drawings

ORGANIC-CHEMICAL COMPOUND WITH ICE-INHIBITORY ACTION

This application is a divisional of application Ser. No. 08/498,972, filed on Jul. 6, 1995, now abandoned which is a divisional of application Ser. No. 08/239,324, filed on May 6, 1994, now abandoned.

BACKGROUND OF THE INVENTION

1. Field of the Invention

It is known that the blocking of interleukin-1β (IL-1β) is an essential step in controlling inflammatory disorders. One possible way of achieving this blocking is to block the formation of IL-1β from the IL-1β precursor. This formation is controlled by the interleukin converting enzyme (ICE). Thus successful blocking or inhibition of ICE would also suppress the formation of IL-1β.

2. DESCRIPTION OF THE RELATED ART

Compounds which act as ICE inhibitors are described in EP 519 748 A2, for example. In this case they are peptide derivatives. It is now of great interest to identify organic chemical compounds which have essentially no peptide structure, as ICE inhibitors. The search for such compounds using appropriate screening methods is, however, complex, and the probability of finding novel indicative structures is correspondingly low.

J. Med. Chem. 37 (1994) 563–564 discloses ICE inhibitors, but these bind irreversibly by particular covalent S—C bonds to the ICE, which may lead to immunological problems.

SUMMARY OF THE INVENTION

It is an object of the present invention to find and characterize organic chemical compounds which are highly effective reversible ICE inhibitors.

We have found that this object is achieved by organic chemical compounds which have structures such that they enter into an interaction with binding sites in a binding cavity, where the binding cavity is defined by at least 22 binding sites and the organic chemical compounds are able to bind to at least 4 or, if at least one covalent bond is formed, to at least 3 binding sites and the spatial position of the binding sites in the binding cavity is defined by coordinates of a right-handed cartesian coordinate system.

DETAILED DESCRIPTION OF THE INVENTION

The coordinates of the 22 binding sites are as follows:

| No of the binding site | | Coordinates of the binding site (in Ångström) | | |
|---|---|---|---|---|
| | | X | Y | Z |
| 1 | | 19.5 ± 0.2 | 1.2 ± 0.2 | 0.6 ± 0.2 |
| 2 | | 16.1 ± 0.2 | 6.2 ± 0.2 | 3.9 ± 0.2 |
| 3 | | 14.2 ± 0.2 | 6.0 ± 0.2 | 1.9 ± 0.2 |
| 4 | | 11.2 ± 0.2 | 2.4 ± 0.2 | 3.5 ± 0.2 |
| 5 | | 6.2 ± 0.2 | 3.5 ± 0.2 | 4.0 ± 0.2 |
| 6 | | 4.5 ± 0.2 | 7.4 ± 0.2 | 7.3 ± 0.2 |
| 7 | | 8.8 ± 0.2 | 8.5 ± 0.2 | 8.0 ± 0.2 |
| 8 | | 10.6 ± 0.2 | 10.2 ± 0.2 | 8.0 ± 0.2 |
| 9 | | 2.9 ± 0.2 | 5.3 ± 0.2 | 7.9 ± 0.2 |
| 10 | | 12.6 ± 0.2 | 9.0 ± 0.2 | 3.9 ± 0.2 |
| 11 | | 5.1 ± 0.2 | 1.7 ± 0.2 | 4.8 ± 0.2 |
| 12 | | 7.2 ± 0.2 | 4.5 ± 0.2 | 0.5 ± 0.2 |
| 13 | | 5.9 ± 0.2 | 6.3 ± 0.2 | 0.3 ± 0.2 |
| 14 | | 6.8 ± 0.2 | 10.1 ± 0.2 | 3.6 ± 0.2 |
| 15 | | 3.8 ± 0.2 | 9.0 ± 0.2 | 2.3 ± 0.2 |
| 16 | | 12.2 ± 0.2 | 7.3 ± 0.2 | 6.9 ± 0.2 |
| 17 | | 16.8 ± 0.2 | 3.6 ± 0.2 | 0.0 ± 0.2 |
| 18 | from | 13.2 ± 0.2 | 7.7 ± 0.2 | 10.1 ± 0.2 |
| | to | 7.5 ± 0.2 | 7.4 ± 0.2 | 12.4 ± 0.2 |
| 19 | from | 19.2 ± 0.2 | 4.8 ± 0.2 | 3.2 ± 0.2 |
| | to | 15.1 ± 0.2 | 0.0 ± 0.2 | 1.0 ± 0.2 |
| 20 | | 0.0 ± 0.2 | 1.0 ± 0.2 | 7.1 ± 0.2 |
| 21 | | 8.9 ± 0.2 | 7.1 ± 0.2 | 4.5 ± 0.2 |
| 22 | | 18.9 ± 0.2 | 4.7 ± 0.2 | 6.4 ± 0.2 | excepting compounds which react as alkylating agents with hydroxyl or mercapto groups to form irreversibly a covalent ether (Enzyme-O—$CR_2$—) or thioether (Enzyme-S—$CR_2$—) linkage, where the group R can be identical or different and are alkyl or H.

The binding sites are preferably each characterized by the types of binding indicated below:

| No. of the binding site | Binding site property |
|---|---|
| 1 | HD or II |
| 2 | HA |
| 3 | HD |
| 4 | HD or II |
| 5 | HD or II |
| 6 | HD |
| 7 | HA |
| 8 | HD |
| 9 | HA |
| 10 | HD |
| 11 | HD or II |
| 12 | HD or II |
| 13 | HD or II |
| 14 | HA or HD |
| 15 | HA or HD |
| 16 | covalent |
| 17 | covalent |
| 18 | HI |
| 19 | HI |
| 20 | HI |
| 21 | HI |
| 22 | HI |

HD: hydrogen bond donor
HA: hydrogen bond acceptor
II = ionic interaction
HI = hydrophobic interaction The compounds should, in particular, have not more than 2 amino acids linked to one another directly via peptide linkages.

The compounds according to the invention preferably have structures such they are able to enter into-a reversible binding, in particular a thiohemiacetal or thiohemiketal linkage, as covalent bond.

The specified binding sites in the binding cavity are derived from the three-dimensional structure of ICE which has been determined for the first time. This spatial structure was determined by X-ray crystallographic analysis.

The organic chemical compounds according to the invention are characterized by their suitability for binding to particular binding sites. The binding cavity should therefore be regarded as a type of binding site framework or negative template with which the compounds according to the invention correlate as positives in the manner defined above and are thus unambiguously defined. The binding cavity as claimed in claim 1 moreover represents in formalized form the actual binding cavity of ICE, with which the compounds according to the invention interact and thus act as ICE ligand or ICE inhibitor.

It follows from this that the binding of the organic chemical compound to ICE becomes better as the number of possibilities for binding of the organic chemical compound to the binding sites, defined above, in the binding cavity increases. However it has emerged that binding to at least 4 or, if at least one covalent bond is formed, at least 3 binding sites leads to a "satisfactory interaction" of the ligand characterized in this way with the ICE.

Preferred organic chemical compounds bind to at least 5 or, in particular, at least 6 or at least 7 binding sites in the binding cavity.

The compounds according to the invention may have a molecular weight of 170–600.

The binding sites are specified by coordinates in Ångström units in a right-handed Cartesian coordinate system. It is thus possible unambiguously to characterize the spatial position of the binding site by the three coordinates x, y and z.

The preferred type of binding between the binding cavity chosen as model in the above sense and the organic chemical compound according to the invention at this site is indicated by the type of binding (H donor binding, H acceptor binding, covalent bond, hydrophobic interaction, ionic interaction).

In the case of binding via hydrogen bond donors or acceptors, indicated by HD and HA respectively, it is moreover possible for an $H_2O$ molecule to be located between the binding site and the compound according to the invention without this influencing the structure of the compound according to the invention.

The hydrophobic interaction defined by binding sites 18 and 19 occurs in a region along a line between the points defined by the two pairs of coordinates in each case, eg. for binding site 18 the line between the point with the coordinates x=13.2±0.2, y=7.7±0.2, z=10.1±0.2 and the point with the coordinates x=7.5±0.2, y=7.4±0.2, z=12.4±0.2. In the case of ionic interactions, the positive charge may be located at the binding site and the negative charge at the compound, or vice versa, according to the invention.

Organic chemical compounds which bind to the specified binding sites consequently also have corresponding affinities for ICE.

The invention also relates to the use of the abovementioned organic chemical compounds for the production of drugs, especially of drugs with an ICE-inhibitory action, and of drugs for controlling inflammatory disorders. Disorders of this type which may be particularly mentioned are: septic shock, rheumatoid arthritis, diabetes and chronic inflammatory bowel diseases.

However, because of the ICE-inhibitory action of the compounds according to the invention they can be used to control all disorders caused by elevated IL-1β levels. IL-1β is known to act on cells which play a part in inflammatory disorders and in wound healing. The compounds according to the invention can therefore be used as drugs for inflammatory disorders such as meningitis, salpingitis and, apart from septic shock, also DIC (disseminated intravascular coagulation) and ARDS (adult respiratory distress syndrome, shock lung). Mention may also be made of arthritis, cholangitis, colitis, encephalitis, endocarditis, giomerulonephritis, hepatitis, myocarditis, pancreatitis, pericarditis and vasculitis. The compounds according to the invention can also be used as drugs for hyperimmune disorders, for immunological rejections and graft-versus-host reactions (GVHR), as well as for autoimmune diseases such as diabetes mellitus and multiple sclerosis. They can also be used as ICE inhibitors for interstitial pulmonary fibrosis, cirrhosis, systemic sclerosis and keloid formation.

The procedure for identifying the organic chemical compounds according to the invention can be as follows: first the binding cavity defined by the binding sites is generated on a computer screen by a conventional operation. Then compounds with their spatial structure are likewise generated on the screen and tested to see whether they bind to at least 3 of the stated binding sites. Once a compound of this type has been identified it is suitable as an ICE ligand.

The same result is obtained when actual three-dimensional models of the binding cavity and the appropriate compounds are made and examined to find whether the required interactions occur, and the compounds according to the invention are identified in this way.

The invention thus also relates to the use of the binding cavity defined by the 22 binding sites indicated above in a method for identifying ICE ligands.

It has emerged that, on testing as ICE inhibitors in appropriate screening systems operating by a quite different method, the compounds according to the invention showed correspondingly positive results in these tests.

It is thus possible to describe the structure of an organic chemical compound suitable as an ICE inhibitor in this case by accurately defining the binding sites to which the compounds according to the invention bind to a binding partner which has been defined for this purpose and is derived from the spatial structure of the target.

One class of compounds defined by the above characterization are the pyridines of the following formulae:

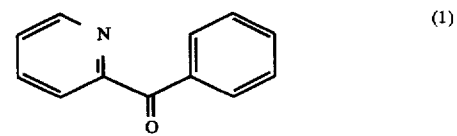

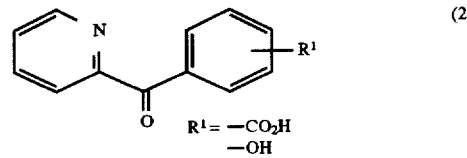

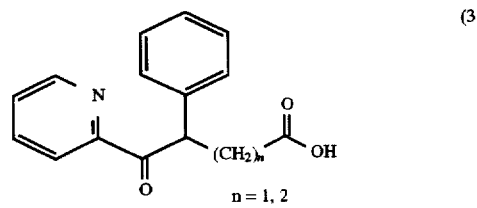

The benzoylpyridines of the general formulae 1 and 2 can be prepared by addition of 2-pyridyllithium onto benzonitrile or suitably substituted benzonitriles of the general formula 4 in an inert solvent such as ether or tetrahydrofuran and subsequent hydrolysis with aqueous acid.

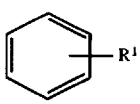

where R is H, COOX or OY, and X is a lower alkyl ($C_1$–$C_6$), preferably methyl, ethyl or tert-butyl, or benzyl. Y is H or benzyl.

The protective group is eliminated by hydrolysis with acid or base or by hydrogenolysis depending on the nature of X and Y.

The preparation of compounds of the general formula 3 preferably starts-from benzonitriles of the general formula 5a, which are converted by reduction in a conventional way into the corresponding aldehydes 5b. The reduction can be carried out simply, for example, using sodium hypophosphite/Raney nickel in pyridine/ acetic acid mixtures as solvent. X in the general formula 5a, b is an ester protective group, preferably tert-butyl.

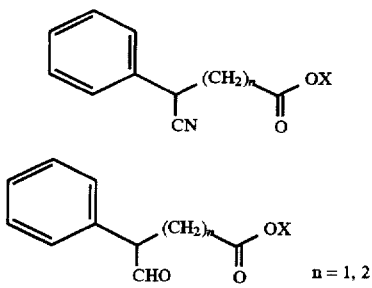

Reaction of the aldehydes 5b with 2-pyridyllithium and subsequent oxidation of the resulting hydroxy compounds, for example with dimethyl sulfoxide/ oxalyl chloride, and subsequent acidic elimination of the tert-butyl protective group results in the required compounds 3.

2-Benzoylpyridine (1) is able to enter into reversible covalent bonding, in the form of a thiohemiacetal linkage, with binding site 16 and a further interaction in the form of a hydrogen bond between the pyridine nitrogen and binding site 4. Together with the hydrophobic interaction of the phenyl ring with binding site 21, this leads to a strong interaction with the enzyme, which is expressed by an inhibition constant in the region of $10^{-6}$ mol/l.

Inhibitors effective in the nanomolar range are obtained by utilizing another interaction, eg. by forming a hydrogen bond or an ionic interaction with binding sites 5 or 6, 7, 12, 13, 14 or 15 in the binding cavity, for example by compounds of type 2 or 3.

The invention finally relates to a process for producing drugs which inhibit interleukin converting enzyme, which comprises identifying a known organic chemical compound by its ability to bind to at least 3 of the 22 binding sites in the binding cavity, and formulating the compound identified in this way with conventional carriers and/or ancillary substances as drug, in particular for controlling inflammatory disorders.

The compounds according to the invention can be administered as drugs in a conventional way orally or parenterally (intravenously, intramuscularly, intraperitoneally).

The dosage depends on the age, condition and weight of the patient and on the mode of administration. As a rule, the daily dose of active ingredient is about 0.1–20 mg/kg of body weight on oral administration and about 0.1–5 mg/kg of body weight on parenteral administration. In the normal case, satisfactory results are obtained with daily doses of 1–10 mg/kg orally and 0.2–2 mg/kg parenterally.

The ICE inhibitors according to the invention can be used in conventional solid or liquid pharmaceutical forms, eg. as uncoated or (film-)coated tablets, capsules, powders, granules, suppositories or solutions. These are produced in a conventional way. The active ingredient can for this purpose be processed with conventional pharmaceutical aids such as tablet binders, fillers, preservatives, tablet disintegrants, flow regulators, plasticizers, wetting agents, dispersants or emulsifiers, solvents, release-slowing agents and/or antioxidants (cf. L. G. Goodman, A. Gilman: The Pharmacological Basis of Therapeutics). The administration forms obtained in this way normally contain the active ingredient in an amount of 50–99% by weight.

We claim:

1. A method of identifying an interleukin converting enzyme inhibitor by determining binding interactions between an organic compound and twenty two binding sites of a binding cavity of an interleukin converting enzyme inhibitor;

said binding sites being defined by the following coordinates in a right-handed cartesian coordinate system:

| No. of the binding site | | Coordinates of the binding site (in Ångström) | | |
|---|---|---|---|---|
| | | X | Y | Z |
| 1 | | 19.5 ± 0.2 | 1.2 ± 0.2 | 0.6 ± 0.2 |
| 2 | | 16.1 ± 0.2 | 6.2 ± 0.2 | 3.9 ± 0.2 |
| 3 | | 14.2 ± 0.2 | 6.0 ± 0.2 | 1.9 ± 0.2 |
| 4 | | 11.2 ± 0.2 | 2.4 ± 0.2 | 3.5 ± 0.2 |
| 5 | | 6.2 ± 0.2 | 3.5 ± 0.2 | 4.0 ± 0.2 |
| 6 | | 4.5 ± 0.2 | 7.4 ± 0.2 | 7.3 ± 0.2 |
| 7 | | 8.8 ± 0.2 | 8.5 ± 0.2 | 8.0 ± 0.2 |
| 8 | | 10.6 ± 0.2 | 10.2 ± 0.2 | 8.0 ± 0.2 |
| 9 | | 2.9 ± 0.2 | 5.3 ± 0.2 | 7.9 ± 0.2 |
| 10 | | 12.6 ± 0.2 | 9.0 ± 0.2 | 3.9 ± 0.2 |
| 11 | | 5.1 ± 0.2 | 1.7 ± 0.2 | 4.8 ± 0.2 |
| 12 | | 7.2 ± 0.2 | 4.5 ± 0.2 | 0.5 ± 0.2 |
| 13 | | 5.9 ± 0.2 | 6.3 ± 0.2 | 0.3 ± 0.2 |
| 14 | | 6.8 ± 0.2 | 10.1 ± 0.2 | 3.6 ± 0.2 |
| 15 | | 3.8 ± 0.2 | 9.0 ± 0.2 | 2.3 ± 0.2 |
| 16 | | 12.2 ± 0.2 | 7.3 ± 0.2 | 6.9 ± 0.2 |
| 17 | | 16.8 ± 0.2 | 3.6 ± 0.2 | 0.0 ± 0.2 |
| 18 | from | 13.2 ± 0.2 | 7.7 ± 0.2 | 10.1 ± 0.2 |
| | to | 7.5 ± 0.2 | 7.4 ± 0.2 | 12.4 ± 0.2 |
| 19 | from | 19.2 ± 0.2 | 4.8 ± 0.2 | 3.2 ± 0.2 |
| | to | 15.1 ± 0.2 | 0.0 ± 0.2 | 1.0 ± 0.2 |
| 20 | | 0.0 ± 0.2 | 1.0 ± 0.2 | 7.1 ± 0.2 |
| 21 | | 8.9 ± 0.2 | 7.1 ± 0.2 | 4.5 ± 0.2 |
| 22 | | 18.9 ± 0.2 | 4.7 ± 0.2 | 6.4 ± 0.2 | said binding sites having the following binding site properties:

| No. of the binding site | Binding site property |
|---|---|
| 1 | HD or II |
| 2 | HA |
| 3 | HD |
| 4 | HD or II |
| 5 | HD or II |
| 6 | HD |
| 7 | HA |
| 8 | HD |
| 9 | HA |
| 10 | HD |
| 11 | HD or II |
| 12 | HD or II |
| 13 | HD or II |
| 14 | HA or HD |
| 15 | HA or HD |
| 16 | covalent |

-continued

| No. of the binding site | Binding site property |
|---|---|
| 17 | covalent |
| 18 | HI |
| 19 | HI |
| 20 | HI |
| 21 | HI |
| 22 | HI | said method comprising:
1) generating the binding cavity defined by the binding sites on a computer screen;
2) generating compounds with their spacial structure; and
3) testing to see whether the compounds bind to at least three of the stated binding-sites;

wherein the interleukin converting enzyme enters into an interaction with binding sites in the binding cavity.

2. The method according to claim 1, wherein the interleukin converting enzyme inhibitor is able to bind to at least 4, or if at least one covalent bond is formed, to at least 3 binding sites in the binding cavity.

3. The method according to claim 1, wherein the interleukin converting enzyme inhibitor is able to bind to at least 5 or, if at least one covalent bond is present, at least 4, preferably at least 6 or, if at least one covalent bond is present, at least 5 of the binding sites.

4. The method according to claim 1, wherein the interleukin converting enzyme inhibitor is able to enter into a reversible linkage as covalent bond.

5. The method according to claim 1, wherein the interleukin converting enzyme inhibitor is able to bind to at least 5 binding sites in the binding cavity.

6. The method according to claim 1, wherein the interleukin converting enzyme inhibitor is able to bind to at least 6 binding sites in the binding cavity.

7. The method according to claim 1, wherein the interleukin converting enzyme inhibitor is able to bind to at least 7 binding sites in the binding cavity.

8. The method according to claim 4, wherein the linkage is a thiohemiacetal linkage.

9. The method according to claim 4, wherein the linkage is a thiohemiketal linkage.

* * * * *